July 24, 1962 C. H. FISCHER Plant Pat. 2,158
GLADIOLUS PLANT
Filed Sept. 1, 1961
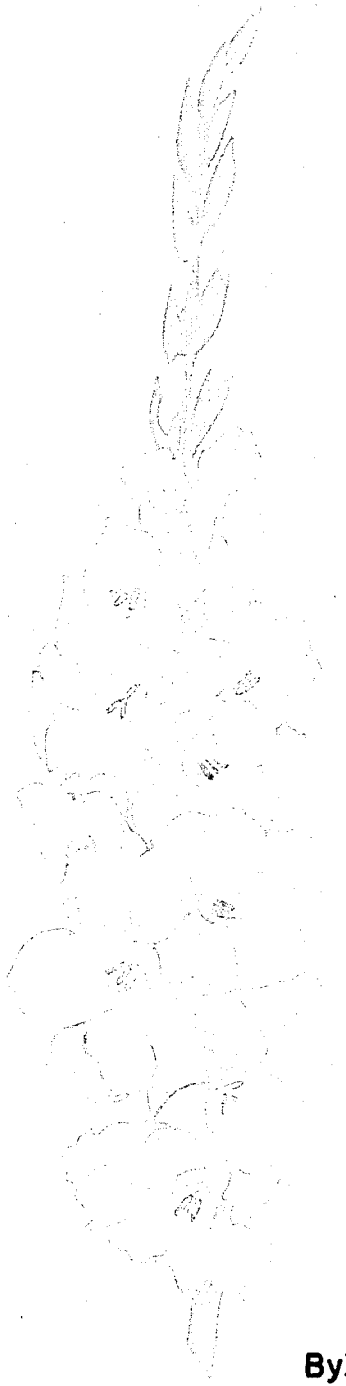
INVENTOR
Carl H. Fischer
By: Lamont Johnston
ATTORNEY United States Patent Office Plant Pat. 2,158
Patented July 24, 1962

2,158
GLADIOLUS PLANT

Carl H. Fischer, St. Charles, Minn., assignor to Selected Glads, Inc., New Albany, Ind., a corporation of Tennessee Filed Sept. 1, 1961, Ser. No. 135,685
1 Claim. (Cl. 47—60)

My present invention relates to a new and improved variety of gladiolus plant and is notable particularly for its delicate color, smooth, round petals, broad inflorescence, uniformity of performance and plant vigor.

To the best of my knowledge, this new variety is the result of a cross between the varieties Beauty's Blush (unpatented) and an unnamed seedling (unpatented) whose parents were Gloaming and Rose O'Day (both unpatented), Beauty's Blush being the seed parent and the seedling the pollen parent. Hand cross pollination was done by me in my field at St. Charles, Minnesota, but no precaution was taken to prevent admixture of other varieties by bees or insects.

The new variety has been asexually reproduced by me in Minnesota by natural increase from cormels through several generations and its characteristics have proven to be permanently fixed.

The illustration, made a part of this application, shows a single bloom spike of this variety, reduced in size, and is as nearly true to color as it is possible to depict. The illustration shows the semi-formal placement of the broad, round florets, and its long, tapering flower-head.

In the following detailed description, color plate references are to the "Horticultural Colour Chart," by The British Colour Council. Where there are other references to color, the ordinary dictionary meanings of the terms are intended.

*The Plant*

Growth: Extremely vigorous, flower spikes averaging 50 to 54 inches in height. Propagates readily.

Blooming: Each spike opens from seven to nine florets about 5 inches in diameter. There are twenty to twenty-four buds per spike. The variety is a mid-season bloomer, coming into bloom in about 85 days from large bulbs.

Stems: Slender and willowy; diameter at base is ½ inch.

Foliage: Healthy green; average leaf is 1 to 1½ inches and the plant foliage is 30 to 36 inches high.

Disease resistance: This variety has been found unusually resistant to Fusarium yellows, Sclerotina dry rot and Septoria leaf spot, to which some other varieties in my fields have been subject, observed when grown as a seedling under irrigation in a black loam soil in the vicinity of St. Charles, Minnesota, under the natural conditions provided by the climate of that area. At the end of the season, it would be found that many other varieties and seedlings had succumbed or been badly affected by the various diseases, whereas this variety remained healthy and unaffected.

Corms: High crowned with thin, papery husks showing a purplish cast where the husk is attached to the bulb and at the top of the bulb. Flesh is Saffron Yellow $7/_3$. Bulbs are round.

*The Flower*

Spike: Tall, willowy; has twenty to twenty-four buds of which four to five open the first day, following which eight to ten are open at one time.

Bud:

*Size.*—Opening buds are about 2½ inches long. Buds taper in size at the tip.

*Opening.*—Eight to ten will show color at one time.

Flower:

*Arrangement.*—Flowers are semi-formally placed in a double row on the stem and usually all face forward.

*Size.*—Individual florets are large, usually measuring 5 inches in diameter. Upper blooms are progressively smaller.

*Form.*—The florets are very round, broad and recurved with raised mid-ribs. Edges of petals are plain with very little frilling.

*Keeping qualities.*—Opens well but bruises easily.

Petals:

*Shape.*—Petals are broad, round, recurved with raised mid-ribs on the inner petals.

*Size.*—Outer petals are 2¼ to 2½ inches across; lip petal is 1½ inches across.

*Aspect.*—Substance is rather thin; surface is smooth and edges are mostly plain-petalled.

*Fragrance.*—None.

*Color.*—Roseine Purple $629/_3$ with flecking $629/_2$ to $629/_1$ on edges of petals. Small white blotch at throat on bottom petals. $629/_1$ at calyx.

Reproductive organs:

*Stamens.*—Purple.

*Pistil.*—Cream.

*Comparisons*

My new variety resembles Pink Chiffon (unpatented) more than any other variety, but differs from it principally as follows:

(1) My variety is a different color from Pink Chiffon.
(2) My variety is more intense in color.
(3) My variety is bluer in color.
(4) My variety has more buds.
(5) My variety produces more plants per bulb.
(6) My variety produces larger bulblets.
(7) My variety is a better grower from bulblets.

Having thus disclosed my invention, I claim:

The new and distinct variety of gladiolus plant, substantially as herein shown and described, characterized by its delicate color, smooth, round petals, broad inflorescence, plant vigor and ease of culture.

No references cited.